United States Patent [19]
Schafer et al.

[11] Patent Number: 6,033,861
[45] Date of Patent: Mar. 7, 2000

[54] METHODS FOR OBTAINING NUCLEIC ACID CONTAINING A MUTATION

[75] Inventors: Alan J. Schafer; Jamie W. Foster, both of Cambridge, United Kingdom

[73] Assignee: Incyte Genetics, Inc., Cambridge, United Kingdom

[21] Appl. No.: 09/193,963

[22] Filed: Nov. 18, 1998

Related U.S. Application Data

[60] Provisional application No. 60/066,206, Nov. 19, 1997.

[51] Int. Cl.[7] .................................................. C12Q 1/68
[52] U.S. Cl. ........................... 435/6; 435/91.1; 536/24.1; 536/25.4
[58] Field of Search ..................... 435/91.1, 6; 536/24.1, 536/25.4

[56] References Cited

PUBLICATIONS

Casna et al., *Nuc. Acids Res.*, vol. 14, 1986, 7285–7303.

*Primary Examiner*—James Ketter
*Attorney, Agent, or Firm*—Incyte Pharmaceuticals, Inc.; Michael C. Cerrone, Esq.

[57] ABSTRACT

In order to facilitate the screening of an organism, or a population of organisms, carrying heterozygous mutations for identifying the presence of a mutation in a gene of interest, a method is provided which utilizes mismatch binding proteins, such as MutS. The method comprises the steps of denaturing double stranded nucleic acid present in a nucleic acid sample from an organism; allowing the nucleic acid to anneal; and removing homoduplexes from the annealed sample, thereby retaining heteroduplexes in the sample. A positive signal from a probe specific for the gene of interest indicates that the organism carries a mutation in the gene.

10 Claims, 5 Drawing Sheets

F1 offspring heterozygous
for paternal mutations

METHODS FOR OBTAINING NUCLEIC ACID CONTAINING A MUTATION

This application claims the benefit of U.S. Provisional Application No. 60/066,206, filed Nov. 19, 1997.

FIELD OF THE INVENTION

This invention relates to the screening of organisms for nucleic acid mutations.

BACKGROUND OF THE INVENTION

It is an object of the invention to facilitate the screening of a population carrying heterozygous mutations in order to identify those members of the population which carry a mutation in a gene of interest.

Where two copies of a gene differ slightly in sequence (e.g. point mutations), their nucleic acid strands can form heteroduplexes (i.e. double stranded nucleic acid containing non-basepaired mismatches). Proteins are disclosed in the prior art which bind heteroduplexes in preference to homoduplexes and these are collectively known as "mismatch binding proteins" (MBPs), e.g. bacterial protein MutS, which binds to mismatches in otherwise complementary nucleic acid duplexes.

WO95/12689 suggests using immobilized MBPs for detecting heterozygosity in a sample from a single organism. This involves incubating amplified DNA with immobilized MBP and then investigating the bound heteroduplexes with labeled probe DNA (see also Wagner et al., 1995, *Nucleic Acids Research*, 23: 3944–3948).

SUMMARY OF THE INVENTION

The invention provides a method for determining whether an organism carries a heterozygotic mutation in a gene of interest, and for selectively enriching a nucleic acid sample of the organism for nucleic acids carrying such a mutation, thereby providing for further characterization of its biological effects.

The invention encompasses a method for preparing a heteroduplex-enriched nucleic acid sample from an organism carrying heterozygous mutations, comprising the steps of denaturing substantially all of the double-stranded nucleic acid present in a nucleic acid sample from an organism, allowing the nucleic acid to anneal under conditions which permit formation of heteroduplexes and homoduplexes and removing homoduplexes from the annealed sample, thereby retaining nucleic acid heteroduplexes in the sample.

As used herein, "substantially all" refers to 96–100%, and typically 98–100%.

As used herein, the term "heteroduplex" refers to a double-stranded nucleic acid molecule that comprises a region of non-complementarity, i.e. a region in which Watson-Crick base pairing does not occur. A heteroduplex will contain a single basepair (bp) mismatch and even up to four basepair mismatches, whether the four are contiguous or individual, single-basepair mismatches.

As used herein, the term "homoduplex" refers to a double-stranded nucleic acid molecule that is 100% complementary, such that Watson-Crick base pairing occurs along its entire length.

At heterozygotic positions in the genome (i.e. one mutant allele and one normal allele), nucleic acid which is denatured and reannealed can hybridize to form heteroduplexes, whereas homozygous alleles (i.e. neither sequence mutated) will form homoduplexes. A heteroduplex will thus be made up of a normal strand and a mutated strand. If homoduplexes are removed from the sample, thereby enriching the sample for heteroduplexes, the sample will represent those alleles in the original sample where one copy was a mutant form.

As used herein, the term "organism" refers to any living being that is genetically diploid, preferably (although not exclusively) one which reproduces sexually.

Preferably, the organism is a mouse.

If the organism carries one mutation in every 1,000 genes, for example, methods of the invention greatly reduce the complexity of each sample (e.g. from 100,000 different sequences to 100 different sequences).

As used herein, "mutation" refers to an alteration in the nucleotide sequence of a gene (including its regulatory sequences) from its wild-type or normal nucleotide sequence which results in the ability to form a heteroduplex with the corresponding normal gene. Thus, the term does not include large-scale deletions or chromosomal rearragements, but does include point mutations and small (1–4 bp) deletions or insertions. This, of course, includes mutations which may be phenotypically neutral, even when homozygous. The range of these "silent" mutations is diverse but, depending on the gene in question, they may comprise mutations in non-coding regions, point mutations which do not alter the function of a codon (e.g. CCU to CCG, or CGG to AGG) and mutations which alter a codon but which ordinarily do not affect the final protein function, such as conservative amino acid substitutions (e.g. CUU Leu to AUU Ile).

Furthermore, whereas the original sample represents both homozygous and heterozygous alleles, the final sample is substantially enriched for heterozygous alleles. Unless two copies of a gene differ (e.g. wild-type and mutant), no heteroduplex will form. While a probe for a gene of interest may hybridize with a sample before homoduplex removal, it will only hybridize with the sample after homoduplex removal if the sample contained two different copies of the gene of interest. A positive signal from the probe therefore indicates that the organism from which the sample was derived carried a mutant copy of the gene of interest.

The nucleic acid sample will typically comprise DNA but may alternatively comprise RNA. DNA is preferably in the form of cDNA, but genomic DNA may also be used. Nucleic acid may be fragmented prior to the annealing or removal steps, preferably such that the fragments are 200–400 bp in size. This can typically be achieved by using a restriction enzyme, although a plurality of restriction enzymes are preferably used to generate overlapping fragments.

It is preferred that the method further comprises, prior to the step of denaturing substantially all of the double-stranded nucleic acid present in a nucleic acid sample from an organism, the step of fragmenting the nucleic acid in the sample.

Preferably, the removal of homoduplexes is effected using immobilized MutS protein.

In a particularly preferred embodiment, the invention provides a method for preparing a heteroduplex-enriched nucleic acid sample from an organism carrying heterozygous mutations, comprising the steps of exposing the germ cells of a first parent organism to mutagenic conditions, mating the first parent organism to a second parent organism to produce an offspring organism carrying heterozygous mutations, denaturing substantially all of the double-stranded nucleic acid present in a nucleic acid sample from the offspring organism, allowing the nucleic acid to anneal under conditions which permit formation of heteroduplexes and homoduplexes and removing homoduplexes from the annealed sample, thereby retaining heteroduplexes in the sample.

According to a further aspect of the invention, there is provided a sample of nucleic acid heteroduplexes obtainable by this method, wherein the frequency of mutation carried in the offspring organism is higher than that of spontaneous mutation.

The invention also encompasses a method for screening a population of organisms carrying heterozygous mutations in order to identify an organism of the population which carries a mutation in a gene of interest, comprising the steps of preparing a plurality of samples of nucleic acid from a corresponding plurality of organisms of a population according to the method described above and contacting the plurality of samples of nucleic acid with a probe specific for the gene of interest so as to identify a mutation in a gene of interest in an organism containing a mutation.

It is preferred that the plurality of organisms comprises 100 or more organisms (e.g., 1,000, 10,000, 100,000, or more).

It is additionally preferred that the samples are affixed at defined positions to a solid support prior to the contacting step. This might take the form, for example, of depositing ('spotting') samples from 10,000 individuals in a 100×100 Cartesian grid on a nitrocellulose membrane, to which they are then fixed.

The probe is specific for the gene of interest and is labeled such that hybridization between the probe and a heteroduplex-enriched nucleic acid sample can be detected. This may be a radioactive label, for instance, or a fluorescent label.

The samples with which the probe hybridizes are derived from an organism carrying a mutation in the gene of interest. It will, of course, be appreciated that while background or non-specific hybridization might occur in samples which are not derived from an organism carrying a mutation in the gene of interest, it will be weaker than the hybridization which occurs with a sample which is derived from an organism carrying a mutation in the gene of interest. The heteroduplex-enriched nucleic acid samples from organisms not carrying a mutation in the gene of interest will, in fact, serve as controls for background or non-specific hybridization, and hybridization above the control level is indicative of a positive result.

For example, on an grid comprising 100×100 samples, the overall frequency of hybridization of samples with a labeled probe (hence, the total signal generated) will be low, but those samples containing mutations in the gene of interest will hybridize to it strongly.

It will be appreciated that the probing step can be adapted for the use of multiple probes. For instance, probes specific for different genes or specific for different regions in the same gene can be used simultaneously.

Where multiple probes are utilized, these are preferably differentially labeled (e.g., differently colored fluorochromes in each probe).

It will also be appreciated that the population need not be screened at the level of the individual. For example, in a population of 10,000 organisms, screening samples from groups of ten individuals could be combined to give 1,000 combined screening samples. These are screened in the same way as the 10,000 would be screened, but the probing results require deconvolution in order to determine which of the ten organisms in a positive combined screening sample carry a mutation. This typically involves screening the ten separate samples which were originally pooled. While combining samples in this way obviously reduces the initial screening effort (e.g. from 10,000 samples to 1,000 samples), the sensitivity of the assay is reduced and the requirement for deconvolution arises. The choice of whether to combine and, if so, how many samples to combine (e.g. 10, 50, 100, etc.) therefore depends on the available resources, the size of the population, the degree of homoduplex removal, etc. This choice can be made without difficulty by the skilled person.

DESCRIPTION

Figure 1:
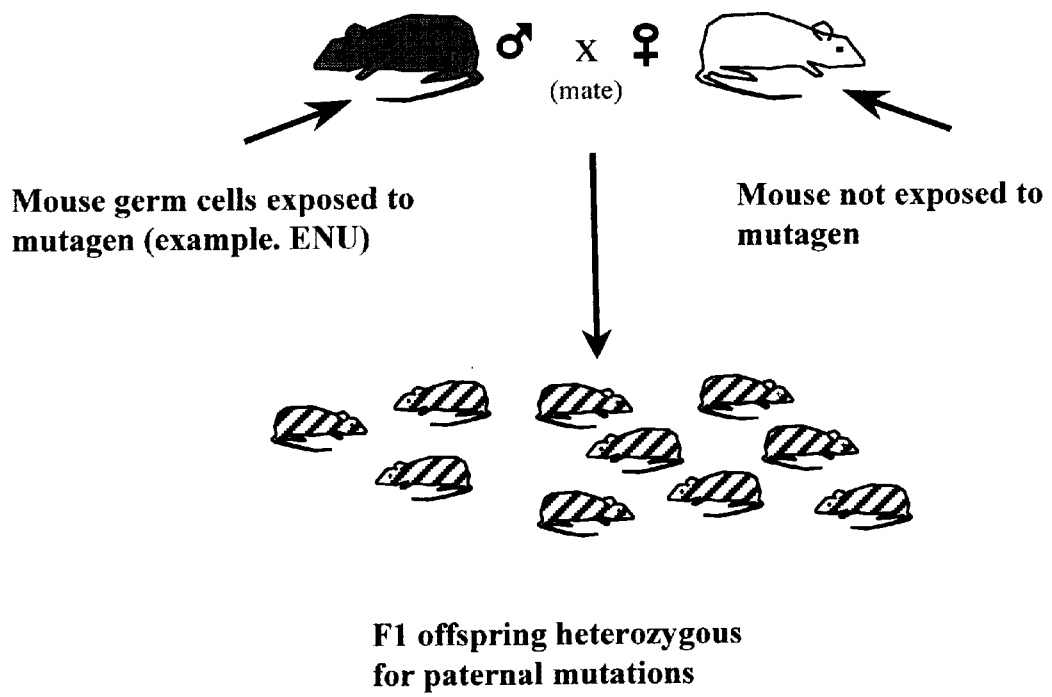
FIG. 1 presents a method for generating mice carrying induced heterozygous mutations.

In order to study the biological effects of genetic mutation, one may use an inbred population whose individuals carry heterozygotic mutations. This population can be screened at a genomic level (e.g., using single-strand conformation polymorphism) in order to determine those individuals which carry a mutation in a given gene (i.e. those which carry one mutant copy population whose individuals carry heterozygotic mutations. This population can be screened at a genomic level (e.g., using single-strand conformation polymorphism) in order to determine those individuals which carry a mutation in a given gene (i.e. those which carry one mutant copy of a gene of interest and one normal copy), even though the effect of the mutation may not be manifested as a phenotype (e.g., a recessive mutation). These individuals can then be bred to create organisms for studies of biological function of a mutation or mutant gene.

To be most useful, the heterozygotic mutant population should satisfy two criteria. First, mutations across the entire genome should be represented. This ensures that the population will contain an individual carrying a mutation for any given gene. Second, for any given gene there should be more than one mutation-carrying individual. This ensures that a diverse range of mutations are available.

These goals can be achieved in two ways: each individual can carry a large number of mutations and/or the population can be large.

A large number of mutations per individual is undesirable due both to increased likelihood of lethality of mutant homozygotes and to the difficulty of deducing the function of a given mutant gene when faced with a phenotype resulting from complex interactions among multiple mutant genes. This means that mutations in genes other than the gene of interest must be removed by selective breeding, the difficulty of which increases in proportion to the number of mutations carried by an individual.

In order to reduce the number of mutations per individual while maintaining the overall number of mutations represented in a population, a larger population (for example, 10,000 mice) is mutated and screened.

Providing a Nucleic Acid Sample

The nucleic acid sample may be derived from any diploid organism. Preferably the organism is an animal, such as an insect, and preferably the animal is a vertebrate, such as a fish or a mammal. Preferred mammals are rodents and humans.

The nucleic acid sample may be derived from various sources. For instance, cDNA may be prepared from an individual's major organs and combined, e.g. to compensate for differential expression patterns. Alternatively, the sample may be derived from a single organ or cell type.

In order to provide sufficient material for screening, rather than preparing nucleic acid from a large number of cells, nucleic acid may be amplified, such as by the polymerase chain reaction (PCR) (see Abramson and Myers, 1993, *Curr. Opin. Biotech.*, 4: 41–47; Zhang et al., 1992, *Proc. Natl. Acad. Sci. U.S.A.*, 89: 5847–51). If amplification is used, it preferably is performed after heteroduplex formation (i.e. after the sample is denatured and annealed) and after heteroduplex removal, due to the infidelity of polymerase-mediated DNA replication in PCR. Any errors introduced in this way can result in the formation of a heteroduplex which may be misinterpreted as being due to the presence of a heterozygotic mutation, or which may reduce detection sensitivity by increasing background noise.

If amplification is used before heteroduplex formation, the amplification products are preferably treated to remove amplification errors (e.g. see WO95/12689).

Preparation of Sample

Denaturation of the nucleic acid sample is performed under conditions which result in complete denaturation of double-stranded to single-strandedness, e.g., via heating of the sample to 100° C. for 5 minutes.

Stringent annealing conditions can be used to eliminate or reduce hybridization between non-allelic loci. During annealing, mutant sequences can hybridize with normal sequences to form heteroduplexes although, of course, re-formation of homoduplexes can also occur between identical sequences (whether mutant or normal).

Removal of Homoduplexes

The degree of homoduplex removal from the sample should be sufficient so that the binding of a probe specific for a sequence of interest which was homozygous in the organism from which the sample is derived is quantitatively reduced. This will typically mean that the abundance of heteroduplexes relative to homoduplexes will be increased by at least two-fold, preferably by at least five-fold, and more preferably by at least ten-fold or greater (e.g., 100-fold).

Homoduplexes may be removed using any reagent which binds to heteroduplexes in preference to homoduplexes (or vice versa) and which does not chemically modify or cleave its bound nucleic acid. MBPs are preferred, such as MutS, along with its derivatives and homologues. The MBP should be immobilized in some way (e.g. WO95/12689). The MBP could, for instance, be attached to a solid support. Suitable solid supports include cellulose, polystyrene, dextran, and nitrocellulose. These may be used in any suitable form, including beads (which may be magnetic), membranes, or columns. The immobilized MBP is able to bind heteroduplexes and retain them on the solid support, while homoduplexes are not retained. The bound nucleic acid may be eluted from the MBP (e.g. Jolly et al., 1997, *Nucleic Acids Res.*, 25: 1913–1919), thus providing a sample which has been enriched for the presence of heteroduplexes, i.e. homoduplexes have been removed. If necessary, the nucleic acid sample may be amplified either before or after elution. If amplification is performed before elution, it typically results in dissociation of the MBP/heteroduplex complex during the denaturing step in PCR.

Preparation of Organism Containing Induced Mutations

An organism carrying heterozygotic mutations can be prepared easily by mating two members of an inbred (therefore, genetically homogeneous) population, one of which parent organisms (and, consequently, its germ cells) has been exposed to mutagenic conditions. The gametes of the mutagenized parent organism will carry mutations which will be transmitted randomly to its progeny, while the other parent organism has not been exposed to mutagen, and will transmit normal chromosomes; therefore, the offspring of such a mating will be heterozygous for every locus at which a mutation was transmitted from the mutagenized parent, having received a normal copy of that sequence from the non-mutagenized parent. It is also possible to mutagenize both parent organisms, although this is less preferable. If a low level of mutation is induced, it is highly unlikely that an offspring will inherit two mutant copies (i.e. homozygous mutations) of any given allele; in that case, mutations are still heterozygotic (i.e. each allele has a mutant and normal copy), but mutations are present in both sets of chromosomes.

Where an organism is said to be "carrying heterozygotic mutations", therefore, it is meant that the genome of the organism (or one or both of its parent organisms) has been exposed to mutagenic conditions and that the mutations which resulted from an exposure are only present on one of the diploid copies such that for every mutant allele, there is also a normal allele.

Typically, an organism "carrying heterozygotic mutations" will not have been exposed to mutagenic conditions itself, but its genome (in the form of half of its chromosomes) will have been. The mutagenesis will have happened to an ancestor, but mutations induced in the genome of the ancestor's germ cells will be inherited by the organism "carrying heterozygotic mutations". This also ensures that any mutations detected in the heteroduplex-enriched nucleic acid sample will be transmitted to offspring by the organism, since the mutations are present throughout the organism's gametes and somatic tissue.

The frequency of heterozygotic mutations carried by the organism reflects exposure to mutagenic conditions; in other words, these mutations occur at a higher frequency than do spontaneous or background mutations, which are characterized by their low frequency of occurrence. The heterozygous mutations should thus be present at a frequency substantially above this background frequency. Suitably, the mutation frequency is such that, on average, in every 50,000 organisms or fewer (e.g., one in every 10,000 organisms, or one in every 1,000 organisms) one mutant copy of a gene occurs which would cause an altered phenotype if bred to homozygosity.

Many suitable methods for inducing mutations are known in the art. These include chemical mutagenesis, radiation, and retroviral or transposon insertion.

Mutagenesis may be performed on whole organisms or on a selected tissue of an organism including but not limited to, for example, mutagenesis of germline cells of an organism, such as sperm stem cells or ova, mutagenesis of embryonic stem (ES) cells of an organism or introduction of a mutant gene into an organism which results in an increased frequency of mutations in the genome. Following mutagenesis of an organism, the organism may be analyzed directly for mutations, or it may be mated and the offspring analyzed for a mutation in a gene of interest. Obviously, it is preferred to analyze offspring in order to ensure that any mutation which is detected can be predictably passed on to further generations. Alternatively, following DNA analysis of a specific tissue for a mutation in a gene of interest, such as mutated ES clones in culture, the cells are transferred to the developing embryo. Mutagens and mutagenesis techniques which are applicable to organisms or cell mutagenesis are described below.

1. Types of DNA mutations.

Mutations in DNA may be (a) large lesion mutations, such as chromosomal breaks, rearrangements, and large insertions or deletions (on the order of kilobases); (b) small lesion mutations, such as cytogenetically visible deletions within a chromosome; and (c) small alterations, such as point mutations, insertions and small deletions (on the order of several-tens of bases). Any type of mutation may be analyzed according to the invention; however, the methods of the invention are preferably applied to mutations which do not result in complete deletion of the gene of interest.

The invention is most useful for detecting the last category of mutations, i.e., point mutations, insertions and small deletions, and therefore it is preferred that the mutagenesis technique used to induce mutations according to the invention induce these types of mutations in a gene of interest.

2. Selection of Mutagenesis Technique.

The selection of a mutagenesis technique useful in the invention is dependent upon several factors. Some mutagens cause a wide spectrum of mutation types at a fixed condition (s). Some mutagens cause different types of mutations depending upon the mutagen dosage, mode of delivery, and the developmental stage at which the mutagen is administered to the organism. In addition, a mutagen may induce mutations at different frequencies depending upon the dosage regimen, mode of delivery, and the developmental stage of the organism or cell upon mutagen administration, all parameters of which are disclosed in the prior art for different mutagens or mutagenesis techniques. In addition, a defect in a gene which in wild-type form prevents mutations from occurring or repairs mutations may result in the failure to repair DNA mutations and thus provide a mutagenized genome for analysis according to the invention. Finally, the mutation rate from tissue to tissue will vary.

A mutagen or method of inducing mutations is considered useful in the invention which provides the highest number of mutations per genome that does not kill the mutated organism.

Therefore, the following guidelines are important for selection of a mutagenesis technique or a mutagen for use in to the invention. First, the number of potentially mutant organisms which are generated for screening must be technically feasible. Second, the type of mutation induced in a gene of interest must leave the gene intact in the genome to the extent that it is detectable as described herein, with small deletions/insertions/substitutions, such as single base pair to several base pairs, being preferred. With these considerations in mind, it is possible to prepare nucleic acid containing heteroduplexes from organisms which have been mutagenized at a high frequency or at a low frequency.

Those mutagens or mutagenesis techniques which result in mutations which occur within a gene, i.e., a region of DNA from which RNA is transcribed, or within the regulatory elements controlling expression of the gene are most useful according to the invention. Chemical mutagens which result in such mutations include, but are not limited to, mutagens which are alkylating agents which cause single nucleotide changes.

Therefore, according to the invention, mutations are induced in an organism at a high enough frequency that the number of organisms needed to screen for a mutation in a gene of interest is not prohibitive. For example, it is useful according to the invention to induce mutations at a high frequency in order to decrease the number of organisms screened. ENU mutagenesis is particularly useful in the invention because, in the offspring of ENU mutagenized male mice, a mutation in any given gene will occur at a frequency of approximately 1 per 1000 mice. Thus, approximately 1000 mice are screened in order to detect a mutation in a particular gene. Although the ratio of 1/1000 has been calculated in the prior art based on phenotypic assays, it is the only way of assessing the relative mutational frequencies of mutagens or mutagenesis techniques useful according to the invention, as direct DNA analysis of the frequencies of mutations induced by a given mutagen or mutagenesis technique has not been performed. Because phenotypic mutation frequencies are based on DNA mutations which alter or destroy the function of a protein such that it causes a phenotypic change, the number of changes in the DNA of these mice in a given gene will be higher than 1/1000 due to "silent" mutations, i.e., which do not result in a phenotypic change. The same type of mutation frequency is obtained using other chemical mutagens, such as MNU, PRC, and MMS. Additional mutagens which may be considered equally useful according to the invention include chlorambucil and melphalan, and those listed below and in Table 1.

Although the mouse is specifically embodied herein as a representative organism that is useful in the invention for inducing mutations and screening for mutations in a gene of interest, the invention is not limited to the use of mice. For example, other rodents such as a rat or hamster also provide representative animal models; however, the invention is not limited to mutagenesis and mutational analysis of a rodent. Non-rodent animals are equally appropriate, for example, organisms such as insects, nematodes, or fish, such as the zebrafish or medaka fish.

The zebrafish is a striped 2-inch long fish from the Ganges River. The zebrafish has been used as a genetic system and conditions for gamma-ray mutagenesis and screening are well-established (Chakrabarti et al., 1983, *Brachydonio Genetics*, 103: 109; Walker and Streisinger, 1983, *Genetics*, 103: 125). The advantages of zebrafish over the mouse for genetic analysis is its small size, the ability to house a large number of animals cheaply, and the large number of embryos produced from one female (usually a few hundred but as many as 1000 eggs). The time from fertilization to gastrulation is only about 5 hours at 28° C.; somites form between 10–20 hours; and by 24 hours postfertilization, a recognizable animal with rudimentary eyes and brain has formed. Thus, the early development of this vertebrate takes only about as long as a phage plaque assay. Rossant et al.( 1992, *Genes Dev.*, 6: 1) describe mutational strategies for mutagenesis of zebrafish, including ENU mutagenesis.

Briefly, a three-generation cross in which F2 females, heterozygous for a number of induced mutations, are backcrossed to their father and mated to their brothers to reveal homozygous mutant phenotypes. A locus-specific mutation frequency of 1/1000 gametes scored is achievable in zebrafish using ENU mutagenesis. Therefore, one needs to screen at least 3,000 mutagenized gametes to approach saturation mutagenesis, and fewer than 2,000 gametes, i.e., on the order of about 1,000 gametes to screen for a mutation in a gene of interest according to the invention. ENU and EMS mutagenesis has been used to induce mutations in isolated sperm from zebrafish (Halpern et al., 1993, *Cell, 75:*

1; and solnica-Krezel et al., 1994, *Genetics*, 136: 1401). The small teleost fish Medaka has also been subjected to ENU mutagenesis (Shiva et al., 1991, *Proc. Natl. Acad. Sci. U.S.A.*, 88: 2545), and also is encompassed within the invention. Zebrafish have been used in large-scale mutagenesis to search for genes controlling development in vertebrates (Mullins et al., 1994, *Curr. Biol.*, 4: 189).

In addition to mutagenized animals, lower organisms are useful according to the invention, such as mutagenized insects, e.g., Drosophila melanogaster. EMS mutagenesis has been performed extensively on Drosophila (Ashburner, 1989, *Drosophila, A Laboratory Handbook*, Cold Spring Harbor Laboratory, Cold Spring Harbor, N.Y.; Grell et al., 1981, Drosophila, *Environ. Mutagen.*, 3: 381; Ondrej, 1971, Drosophila melanogaster, *Mut. Res.*, 12:159). Non-insect primitive organisms such as the roundwormn, Caenorhabditis elegans, may also be used according to the invention. EMS has been used to mutagenize C. elegans (Wood, 1988, *The Nematode C. Elegans*, Cold Spring Harbor Laboratory, Cold Spring Harbor, N.Y.).

Non-mammalian organisms, such as fish, nematodes, and insects, are particularly useful according to the invention in identifying mutations in genes which are suspected to play a role in early development of the organism, e.g., in embryonic development, such as pattern-forming genes, limb-forming genes, or organ-forming genes.

From the above description, it is evident that, in order to be useful in generating heteroduplexes to be isolated and detected according to the invention, mutations also may be induced in an organism at a lower frequency (for example, where a mutagen is used having a lower mutation-induction frequency), provided a higher number of organisms or tissue samples from organisms are screened for a mutation in a gene of interest. The number of organisms tested is generally limited by the following: the number of mutant organisms that are generated, and the number of organisms that are screened. It may be possible to generate and screen a sufficient number of organisms to detect even an exceedingly low frequency of mutation, e.g., 1 mutation/50,000 organisms–1/75,000. Although screening for mutations which occur at a given frequency may be labor-intensive, a screening procedure must be employed which is feasible.

The invention therefore contemplates the use of any type of mutagenesis technique, including chemical mutagenesis, radiation mutagenesis, and to mutagenesis techniques which are based on molecular biology, such as introduction into an organism of a gene encoding a defective DNA repair enzyme, retroviral insertion mutagenesis and promoter- and gene-trapping mutagenesis, as described below.

The invention is particularly useful where the mutagenesis results in germline mutations in a parent organism, i.e., which are passed onto offspring from which heteroduplex-enriched nucleic acid samples are prepared and tested for the presence of mutations in genes of interest.

A mutagenesis technique which confers a mutation rate in the range of 1 mutation per 500 genes–1 mutation per 10,000 genes, or 1 mutation per gene per 100 organisms–1 mutation per gene per 10,000 organisms, optimally at least 1 mutation per 1000 genes, or 1 mutation per gene per 1000 organisms is useful in the invention. It is desired according to the invention that the mutation frequency possess an upper limit that is below the frequency of inducing a dominant lethal mutation in every organism.

A) Chemical Mutagenesis and Mutagens.

Chemical mutagens are classifiable by chemical properties, e.g., alkylating agents, cross-linking agents, etc. The following chemical mutagens are useful according to the invention. The following four mutagens are particularly useful for mutagenesis of male germ cells:

N-ethyl-N-nitrosourea (ENU)

N-methyl-N-nitrosourea (MNU)

procarbazine hydrochloride chlorambucil

Other chemical mutagens which are useful are as follows:

cyclophosphamide methyl methanesulfonate (MMS)

ethyl methanesulfonate (EMS)

diethyl sulfate acrylamide monomer triethylene melamin (TEM)

melphalan nitrogen mustard vincristine dimethylnitrosamine

N-methyl-N'-nitro-Nitrosoguanidine (MNNG)

7,12 dimethylbenz(a)anthracene (DMBA)

ethylene oxide hexamethylphosphoramide bisulfan

TABLE I

Specific-locus mutation rates induced by chemicals that are mutagenic in post-cell stages of spermatogenesis

| Chemical | Ref. | Period of maximum effect. days(4) | Exposure(2) | | Induced mutation rate(1) per locus | | Lethal(3)/tested mutations |
|---|---|---|---|---|---|---|---|
| | | | mg/kg | mol × $10^{-5}$ | × $10^{-5}$(5) | per mol | |
| Cp | A | 1–14 | 120 | 46.0 | 24.3 | 0.5 | 3/5 |
| McMs | B | 5–12 | 40 | 36.3 | 24.0 | 0.7 | 10/14 |
| EtMs | B | 5–12 | 175 | 141.0 | 20.9 | 0.1 | 0/1 |
| $Et_2SO_4$ | C | 5–12 | 200 | 129.7 | 11.2 | 0.1 | 4/4 |
| AA | I | 8–14 | 250 | 351.6 | 18.2 | 0.1 | 1/2 |
| TEM | D | 8–21 | 0.2 | 0.1 | 33.9 | 346.2 | 7/8 |
| ChI | I | 15–21 | 10 | 3.3 | 127.3 | 38.7 | 1/4 |
| Prc | E, F | (8) | 600 | 232.8 | 21.6 | 0.1 | 1/4 |

TABLE I-continued

Specific-locus mutation rates induced by chemicals that are
mutagenic in post-cell stages of spermatogenesis

| Chemical | Ref. | Period of maximum effect. days(4) | Exposure(2) mg/kg | mol × $10^{-5}$ | Induced mutation rate(1) per locus × $10^{-5}$(5) | per mol | Lethal(3)/tested mutations |
|---|---|---|---|---|---|---|---|
| ENU | G | 32–38 | 50 | 42.7 | 10.6 | 0.2 | 0/5 |
| MNU | H | 36–42 | 75 | 72.7 | 90.2 | 1.2 | 0/17 |

Cp, cyclophosphamide; MeMS, methyl methanesulforate; EtMs, ethyl methanesulforate; $Et_2SO_4$, diethyl sulfate; AA, acrylamide monomer; TEM, triethylene melamine; ChI, chlorambucil; Prc, phocarbazine hydrochloride; ENU, N-ethyl-N-nitrosourea; MNU, N-methyl N-nitrosourea.
(1)Expressed per kg of body weight. When results for more than one exposure level of a chemical were available, we list the one that the investigator(s) found most suitable for generating mutation-rate data.
(2)Experimental minus historical control, 43/801, 406, for period of maximum response.
(3)Lethals excluded. For chlorambeuil, the number includes mutations for which there is genetic, cytogenetic, and/or molecular evidence for deletion.
(4)Postexposure.
(5)Number of mutations in sample is shown in parentheses.
(8)Experiment did not involve sequential matings.

References:
A. Ehling, U. H. & Neuhauser-Klaus, A., 1988, *Mut. Res.*, 199, 21–30.
B. Ehling, U. H. & Neuhauser-Klaus, A., 1984, in *Problems of Threshold in Chemical Mutagenesis*, eds. Tazima, Y., Kondo, & Kuroda, Y. (Environ, Mutagen. Soc. Jpn., Mishima, Japan), pp. 15–25.
C. Ehling, U. H. & Neuhauser-Klaus, A., 1979, *Mut. Res.*, 59: 191–198.
D. Cattanech, B. M., 1967, *Mutat. Res.*, 4: 73–82.
E. Ehling, U. H. & Ncuhauser-Klaus, A., 1979, *Mut. Res.* 59: 245–256.
F. Kratochvilova, J., Pavor, J. & Neuhauser-Klaus, A., 1988, *Mut. Res.*, 198: 295–301.
G. Russell, W. L. & Hunsicker, P. R., 1983, *Environ. Mutagen.*, 5: 498 (abstr.).
H. Russell, W. L. & Hunsicker, P. R., 1984, *Environ. Mutagen.*, 6: 390 (abstr.).
I. Russell et al., 1989, *Proc. Nat. Aca. Sci. U.S.A.*, 86: 3704.

ENU Mutagenesis in Particular

One particularly useful mutagen according to the invention is the chemical mutagen ethylnitrosourea (ENU). ENU may be used to induce genomic mutations in any organism, including but not limited to lower organisms such as insects and worms, as well as higher organisms such as vertebrates, e.g., mammals, e.g., rodents such as mice and rats, hamsters, primates, and zebra fish, cows, sheep, pigs, and dogs. Mutagenesis and DNA mutation screen also may be applied to other organisms which are used as model systems for human disease. Rats are a good candidate for practical reasons, i.e., since mouse-based animal facilities are able to breed and maintain rats. The inventive methods are easily applicable to the rat and provides a method for producing and identifying mutations in specific rat genes.

Described below is the applicability of ENU mutagenesis of mice.

The animals are housed in a mouse facility which conforms to government regulations for animal care. There are several veterinarians who supervise and monitor the animal welfare. C3H male mice are injected interperitoneally with ENU. We have about 150 males injected every 3 weeks to provide breeding stock. They are mated with either one or two untreated females in a cage (a plastic box with wire lid). Approximately every other day, the males are put in with new females, each of which will have 5–6 offspring (F1). The females are pregnant for 3 weeks (21 days) and after birth, the offspring are kept with their mothers for 3 weeks, at which time they are weaned and a little clip of tail is taken before the offspring are transferred into single sex cages (boxes), each housing 6–7 mice. The tail clip is taken at this time because mice of that age do not react to the clip; apparently there is no pain. At later ages they do react, and would need anesthetic. At earlier ages the tail is smaller, yielding less DNA. Also it is convenient, as at weaning the mice are given a unique identifying number and are being handled anyway for transfer to another cage. A room holds about 300 cages, with roughly 1750 mice per room. Hexagen has six such rooms. The population of mice is kept at ~10,000 (there are 8000 now, but will be 10,000 in July). Once at 10,000 population, 2,000 new arrive each month and the 2,000 oldest (aged 5 months) depart. This is done because virgin female mice will not mate after a few months, although we can always obtain eggs from them and use IVF to recover. Male mice also lose interest in mating after approximately 9–12 months.

Experiments in which mutagenesis was induced by the chemical mutagen ENU have used in excess of 500,000 mice. The genes involved were assayed indirectly by observation of phenotypic changes in the mice. ENU is believed to produce mutations at random throughout the genome, and the frequency of mutations, determined for numerous genes, is in the range of 0.5–1.5 mutant mice per 1000 mice, irrespective of the gene screened. In the past, the presence of mutations could only be inferred on the basis of a phenotype in the mutated mice. Most of these mutations do not produce an obvious phenotypic change in the heterozygous state and required additional breeding to make the mutations homozygous (F2 and F3 generations) to observe the effect of the mutation. Mutagenesis and the preparation of heteroduplex-enriched nucleic acid samples according to the invention does not require a previously-determined mutant phenotype, as the F1 generation mouse DNA is analyzed directly for the presence of a mutation in the gene of interest. In 1000 mice, 0.5–1.5 mutations in any gene may be detected. By screening 10,000 mice, it is possible to identify 5–15 mice, each carrying heterozygous mutations in a target gene. Any number of genes can be screened in these same 10,000 mice. Assuming 100,000 genes in a mammalian genome, then each mutagenized mouse is carrying mutations in one copy of approximately 100 different genes. The additional mutant genes in each mouse are easily removed by breeding. ENU mutagenesis of mice is performed as described in Example 1.

Using ENU mutagenesis, it is expected that the gene of interest will be mutated to produce a phenotype once in 1000 mice. If a given animal genome contains, for example, 100,000 genes, then each ENU mutated animal will contain in its ENU mutated genome one protein-altering mutation in one allele of every 100 genes.

ENU mutagenesis also may be carried out on rats, following a procedure similar, if not identical to ENU mutagenesis of mice.

ENU mutagenesis also may be carried out on zebrafish, as described herein for ENU mutagenesis of mice.

B) Radiation Mutagenesis.

In general, Xrays, gamma rays, neutrons, etc., cause DNA breakage. Cellular repair mechanisms of DNA breaks result in regions of DNA which contain large lesions, including rearrangements and deletions. Although analysis of other types of mutations are preferred according to the invention, analysis of radiation induced mutations, which tend to be larger in that they encompass more bases, are also encompassed by the invention.

UV light-induced mutations are largely single nucleotide alterations. However, because UV light does not penetrate an animal, it is used for inducing mutations in cells in culture, including embryonic stem (ES) cells, or on exposed tissues of an animal, e.g., eyes, skin.

In addition to chemical or radiation induced mutations, mutations may be induced in an animal using insertional mutagenesis techniques, as follows.

C) Retroviral Insertion Mutagenesis

Retroviruses can be used to cause insertional mutations, and retroviral insertions are usually simple and cause little or no alteration in surrounding host DNA. Retroviral vectors are easy to use, infect a wide variety of cell types, including ES cells, are stable through multiple generations, and do not cause rearrangements of the host genome when integrated. The mutation frequency from retroviral insertion is estimated at about 1 mutation/$1.5 \times 10^6$ cells (Keuhn et al., 1987, *Nature*, 326: 295). (For retrovirally induced mutations in the mouse, see Harbers et al., 1984, *Proc. Nat. Aca. Sci. U.S.A.*, 3: 162; Soriano et al., 1987, *Genes Dev.*, 1: 366; and Gridley et al., 1987, *Trends in Genetics*, 109: 235).

Untargeted retroviral insertion mutagenesis is performed on ES cells as follows. Briefly, ES cells are transfected with a retrovirus which integrates into the genome at random (e.g., 1 integration per genome). If the insertion lands in a gene or control element of a gene, the insertion will result in inactivation of the gene. Mice may be made from the ES cells and the mutation is introduced into the germ line for breeding. A detailed description of retroviral insertion mutagenesis is found in *Methods in Enzymology*, vol. 225, 1990.

D) Promoter- or Gene-Trapping Mutagenesis

Entrapment vectors, first described in bacteria (Casadaban and Cohen, 1979, *Proc. Nat. Aca. Sci. U.S.A.*, 76: 4530; Casadaban et al., 1980, *J. Bacteriol.*, 143: 971) permit selection of insertional events that lie within coding sequences. Entrapment vectors can be introduced into pluripotent ES cells in culture and then passed into the germline via chimeras (Gossler et al., 1989, *Science*, 244: 463; Skarnes, 1990, *Biotechnology*, 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed. Enhancer traps have a minimal promoter which requires an enhancer to function, and contains a reporter gene. If the vector inserts near an enhancer, then the reporter gene is expressed.

The vector may be introduced into the ES cells by electroporation or using a retrovirus. Activation of the reporter gene can only occur when the vector is within an active host gene and requires generation of a fusion transcript with the host gene. The reporter gene activity then provides an easy assay for integrations in expressed genes. These DNA integrations are highly mutagenic because they interrupt the endogenous coding sequence. It is estimated that the frequency of obtaining a mutation in some gene of any in the genome using a promoter or gene trap is about 45%. A detailed description of retroviral insertion mutagenesis is found in *Methods in Enzymology*, vol. 225, 1990.

E) Mutagenesis as a Result of Deficiency of a DNA Repair Enzyme

The invention encompasses mutagenesis as a result of a deficiency in a DNA repair enzyme; i.e., the presence in an organism of a mutant gene encoding a mutant DNA repair enzyme is expected to generate a high frequency of mutations (i.e., about 1 mutation/100 genes–1 mutation/10,000 genes) in the genome of the organism to be useful according to the invention. DNA repair enzymes include but are not limited to topoisomerases, helicases, and recombinases. Examples of genes encoding DNA repair enzymes include but are not limited to Mut H, Mut S, Mut L, and Mut U, and the homologs thereof, including mammalian homologs. Such homologs include MSH 1-6, PMS 1-2, MLH 1, GTBP, and ERCC-1.

McWhir et al. (1993, *Nature Genetics*, 5: 217) describe a mouse containing a defective DNA repair enzyme resulting from a mutation in the DNA repair gene ERCC-1. In nucleotide excision repair, damaged bases are removed with adjacent residues as an oligonucleotide and the resulting gap is then patched by repair synthesis. ERCC-1 is required for the incision step necessary to remove damaged DNA. Mice were generated containing the defective gene by targeting the excision repair cross complementing gene ERCC-1 in the embryonic stem cell line, HM-1. Homozygous ERCC-1 mutants died before weaning; however, heterozygous ERCC-1 mutants survived and were available for mating. It is contemplated according to the invention that a mammalian organism heterozygous for a mutant gene encoding a DNA repair enzyme may be used to screen for a mutation in a gene of interest.

Where the organism is not an animal, the mutagenesis and breeding procedures is adapted as necessary. For instance, to produce a mutant population of plants, it may be desired to mutagenize pollen, which can then be used to produce a suitable plurality of mutagenized organisms. The totipotency of plant cells also facilitates the generation of further organisms carrying a mutation of interest, both heterozygotes and homozygotes.

EXAMPLE 1

Figure 2:
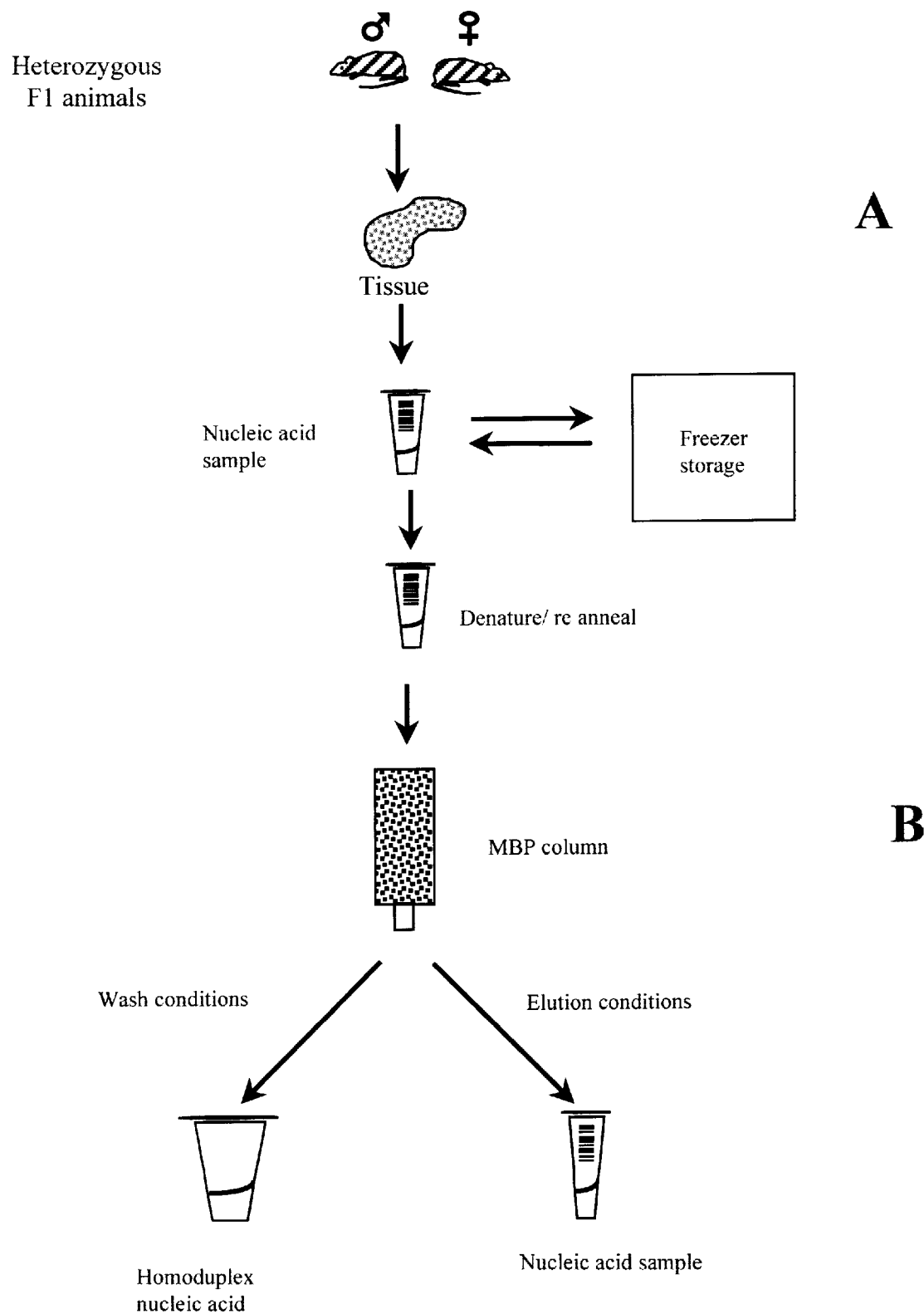
FIG. 2 illustrates how heteroduplex-enriched nucleic acid samples from mice provided as in FIG. 1 are prepared.

Screening a Population for Mutations According to the Invention i. Generation of Mice Carrying Heterozygotic Mutations Random mutations were induced in the genome of premeiotic spermatogonia of 300 male mice (strain C3Heb/Fej) using ethylnitrosourea (ENU). Three separate doses of 100 mg/kg body weight ENU were injected interperitoneally at intervals of one week. Approximately one third of the mice were rendered permanently sterile, but after 8–14 weeks, the other two thirds were mated with two non-mutagenized females each, producing F1 offspring carrying heterozygous mutations in the genome of their somatic and germ tissue (see FIG. 1). About 1000 F1 offspring were generated per week by this method.

ii. Extraction of Nucleic Acid (FIG. 2A)

A 200 µl blood sample and a short tail-clipping were taken from 3000 F1 mice, aged 6 weeks. For each sample from each mouse, RNA and genomic DNA were extracted separately using standard protocols (Sambrook et al., 1989, *Molecular Cloning. A Laboratory Manual.*, 2nd Edition, Cold Spring Harbor Laboratory Press, Cold Spring Harbor, N.Y.). The RNA was converted to double-stranded CDNA with reverse transcriptase.

10 µg DNA from each F1 mouse was digested using Sau3AI in a total reaction volume of 30 µl (manufacturer's recommended concLitions). Following digestion, the DNA was precipitated by the addition of 3 µl sodium acetate (3.0M) and 80 µl ethanol. The DNA was collected at the bottom of the reaction tubes by centrifugation at 15,000 g for 30 minutes and the ethanol was aspirated and discarded. The nucleic acid was denatured and re-annealed using the phenol enhanced re-association technique (PERT) (Miller and Riblet, 1995, *Nucleic Acids Res.*, 23: 2339–2340), a technique suitable for reducing hybridization between non-allelic sequences. The restriction digested, double-stranded DNA samples were resuspended in 50 µl PERT buffer (1.5M sodium thiocyanate, 120 mM sodium phosphate, 10 mM EDTA, 8% phenol) and denatured by heating to 100° C. for 10 minutes and quickly chilled on ice to form an emulsion. The samples were then placed in a programmable thermal cycler and continuously cycled for 24 hours, with each cycle comprising steps of 65° C. (2 minutes) and 37° C. (15 minutes). The samples were centrifuged at 15,000 g for 10 minutes and the upper phenol phase removed and discarded. The DNA was precipitated by adding 5 µl sodium acetate (3.0M) and 125 µl ethanol and pelleted by centrifugation at 15,000 g for 30 minutes. After the ethanol was aspirated and discarded, the DNA was resuspended in 20 µl mismatch binding protein (MBP) reaction buffer (20 mM Tris-HCI, pH 7.6, 5 mM $MgCl_2$, 0.1 mM dithiothreitol, 0.01 mM mM EDTA) with the addition of 3% BSA.

Each sample was given an identifier, so that the mouse from which any particular sample was derived could be traced, and the digested nucleic acid samples were stored.

iii. Homoduplex Removal (FIG. 2B)

Disposable MBP columns were prepared by applying 500 ng MutS protein (Amersham; UK) to nitrocellulose columns in 50 µl NIBP reaction buffer. The DNA samples were removed from storage, applied to the columns and incubated at room temperature for 30 minutes to allow heteroduplex DNA molecules to be bound by the MutS MBP. Unbound homoduplex molecules were removed from the column by five washes of 200 µl MBP reaction buffer. Bound heteroduplex DNA molecules were eluted by incubating the column at 37° C. for 30 minutes in 50 µl elution buffer (100 mM Tris-HCI, 150 mM NaCl, 100 ug/ml proteinase K). Eluted DNA was precipitated by the addition of 5 µl sodium acetate (3.0M) and 125 µl ethanol and collected at the bottom of the reaction tube by centrifugation at 15,000 g for 30 minutes, after which the DNA pellet was resuspended in 10 µl TE (10 mM Tris-HCl, pH 7.5,1.0 mM EDTA).

This eluted heteroduplex DNA could have been used in screening according to the invention; however, the amount of DNA in the blood samples was lower than that in the tail-clippings, thereby reducing the quantity of heteroduplex DNA which was recovered from each sample. To compensate for this, the MBP-treated blood-derived nucleic acid samples were subjected to whole genome amplification [Zhang et al., 1992, supra] to give a minimally-biased linear amplification of the complete nucleic acid used as the starting material. A 5 µl aliquot from each sample was placed in a reaction tube containing the whole genome amplification reaction components (100 mM Tris-HCl, pH 8.9, 150 mM KCl, 200 µM each [dCTP, dATP, dGTP, dTTP], 40 mM random 15-mer, 1.25U Taq polymerase) and the samples were placed in a thermal cycling machine and cycled [94° C. 1 minute; 37° C. 2 minutes; 37°–55° C. ramp at 10 seconds/degree; 55° C. 4 minutes; 50 cycles], followed by a final incubation at 72° C. for 5 minutes.

Figure 3:
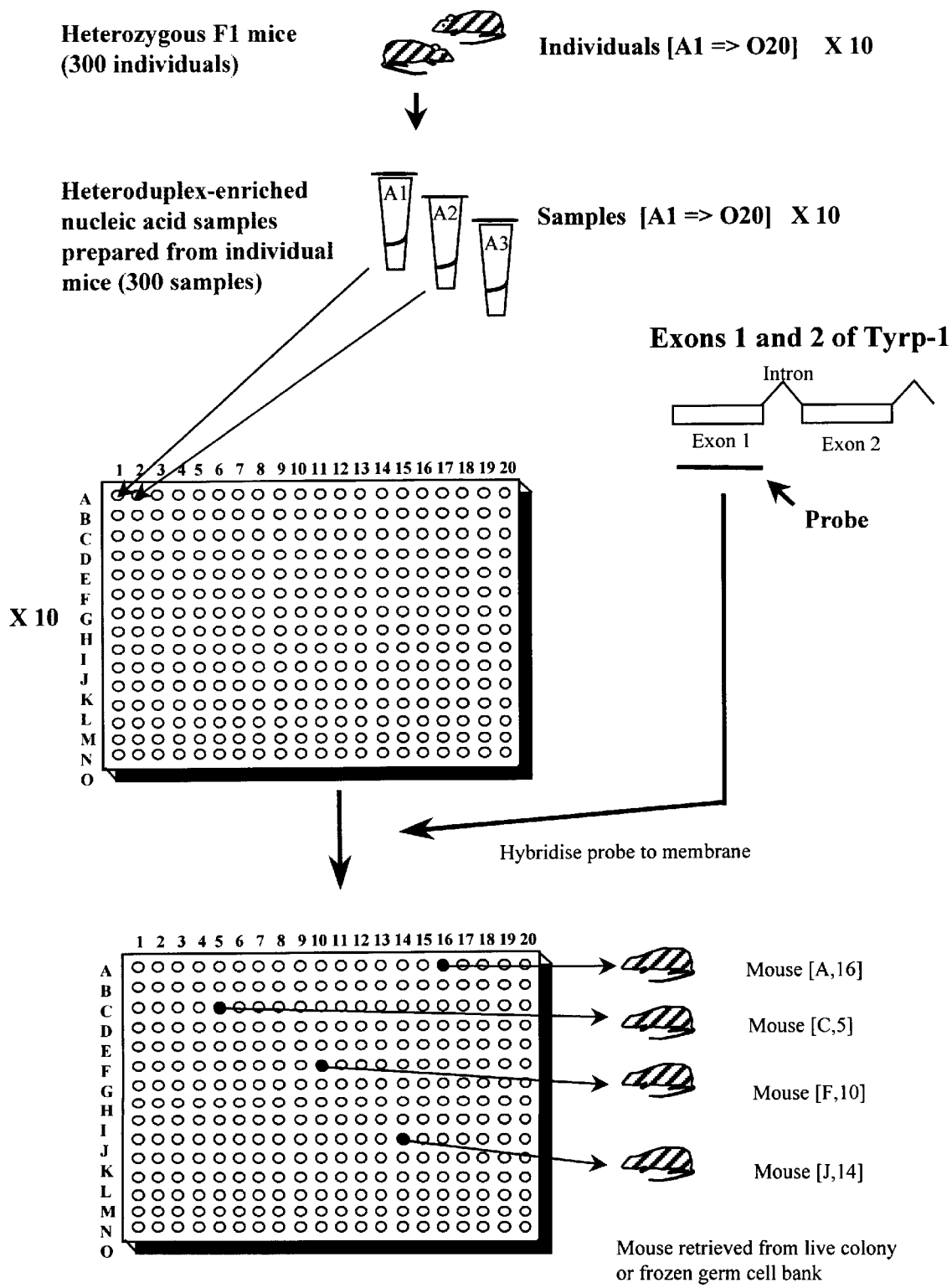
FIG. 3 demonstrates how a population of 10,000 of these mice are screened to identify those members of the population which carry a mutation in the first exon of gene X.

This amplified, heteroduplex-enriched DNA sample was then used in screening, as described below.

iv. Screening the Population (FIG. 3)

The heteroduplex-enriched nucleic acid samples were used in order to find F1 mice which carried mutations in genes of interest. Because of the size of the population, it was anticipated that there would be more than one mouse carrying a mutation in any given gene, resulting in an allelic series of mutations spread throughout the coding and non-coding regions. In order to aid studies of the function of a gene, these mutations would preferably affect the function of the protein in different ways.

One gene of interest was the Tyrosine related protein-1 (Tyrp1; Genbank accession number X03687), a melanocyte-specific enzyme involved in melanin synthesis. Recessive mutant alleles in mice cause a brown coat color, while a dominant allele causes an almost white appearance in black mice. Mutations in the first exon of the tyrp gene were screened.

1 µl of each of the 3000 heteroduplex-enriched nucleic acid samples was deposited ('spotted') on nylon hybridization membranes in a grid pattern using a robotic fluid handling device (10 sheets; 300 samples per sheet: A1, A2, . . . , O,19, O,20). The nylon membranes were placed on absorbent paper soaked in 0.4M NaOH, simultaneously denaturing the screening samples and fixing them to the nylon membranes.

A probe was produced by PCR amplification of the first exon of the gene from an untreated C3Heb/Fej mouse, using a pair of specific primers which were designed using the PCR primer design program Primer-3.0. This DNA was radio-labeled using a Multiprime™ kit (Amersham; UK) incorporating $^{32}P$-dCTP, and hybridized to the heteroduplex-enriched nucleic acid samples on the nylon membranes.

The membranes were washed under stringent conditions (0.2×SSC, 0.2% SDS; 65° C.) to reduce non-specific hybridization and then exposed to X-ray film. While a low level of radioactivity was visible across the whole film (background hybridization), four dark spots were apparent on one of the autoradiograms, which were indicative of the probe being retained preferentially where there were complementary sequences. These spots were at positions A16, C5, F10 and J14 in the grid, indicating that the mice which gave rise to these four samples carried heterozygotic mutations in the first exon of the Tyrp1 gene.

These four mice were selected from the population and are being subjected to phenotypic analysis. This will, of course, only identify phenotypes if the particular mutation is dominant. Consequently, the mice are also being used for breeding in order to obtain mice carrying homozygous mutations for detailed functional characterization. As the F1 are heterozygous for mutations, only half of the F2 mice inherit the Tyrp mutation from the parent and so, for the mutations to be rendered homozygous, F3 progeny must be produced. In the course of breeding to further generations (F4, F5, etc.), other mutations carried by the mice will be removed selectively, which will ensure that phenotypic interactions between these mutations and a mutation in the gene of interest do not interfere with functional analysis of that gene.

Each of the mutations which were detected was characterized in detail; the first exon of the Tyrp1 gene from each mouse was amplified by PCR and then sequenced on an ABI automated sequencing machine. At one position in each sequence, two sequencing peaks were observed, indicating that two different alleles were present. The four mutations were distributed across the first exon, giving an allelic series of mutations, albeit a small one.

Creating an allelic series of mutations in a mouse using traditional transgenic methods would have been very labor-intensive and time consuming. Screening the population of heterozygous mutant mice was far less onerous and gave satisfactory results.

Figure 4:
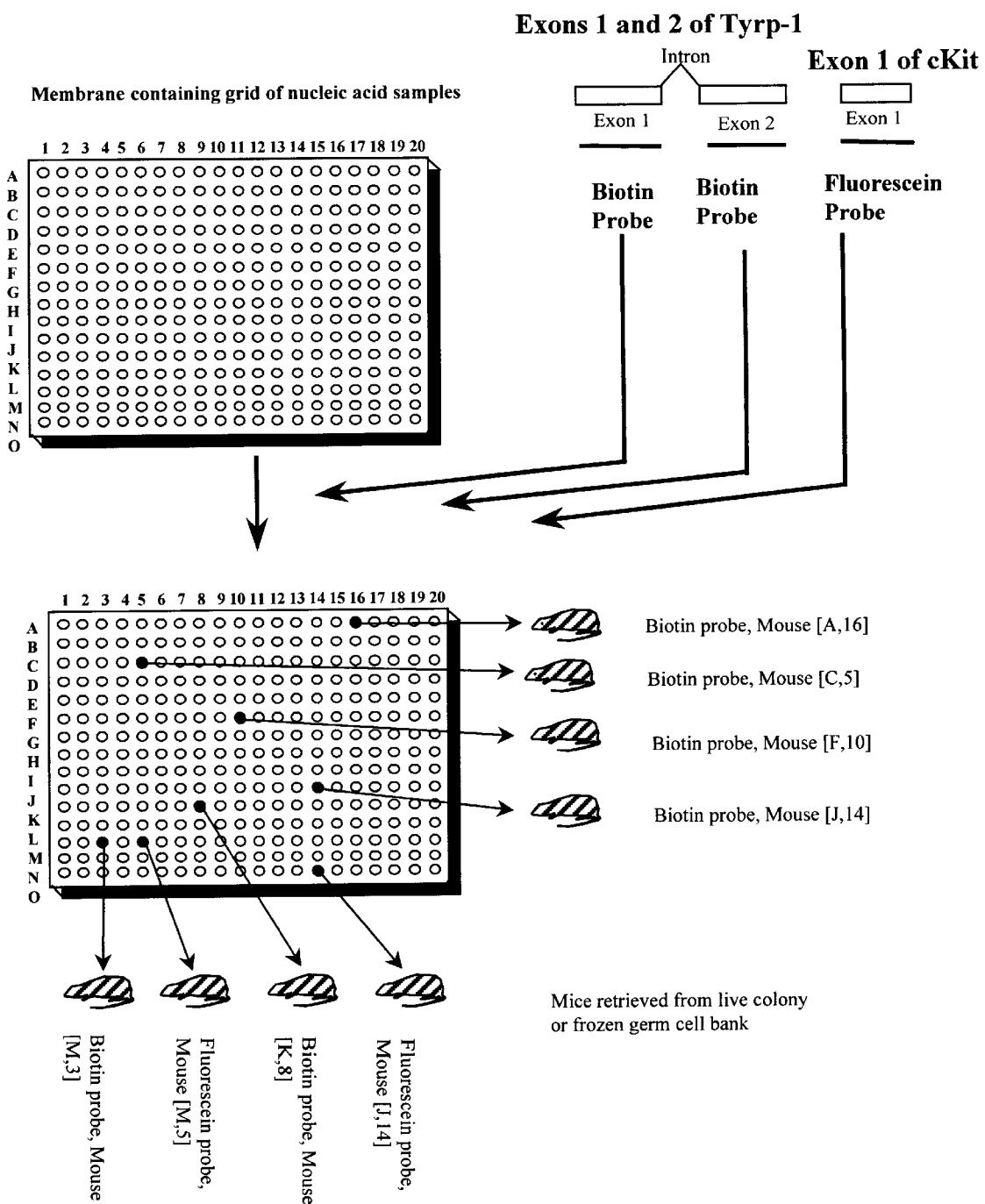
FIG. 4 demonstrates the screening of the population for mutations across the whole length of gene X.

EXAMPLE 2
Simultaneously Screening Different Genes) (FIG. 4)

The gene encoding mast cell growth factor (MGF in mice; known as stem cell factor (SCF) in humans) was also screened by the method of the invention. MGF is the ligand for the c-kit tyrosine kinase receptor (in humans, c-KIT) and is a haematopoetic growth factor critical to growth of several distinct cell lineages. Mutations in MGF, or in c-kit, can affect the ligand/receptor interaction such that signalling is no longer triggered; mutations which have no such effect are also useful, since they car, be used to map regions of the protein which are not critical for function. Dominant mutations of the MGF and c-kit genes in mice affect germ cell development, coat color and hematopoiesis; mutation of human c-KIT can cause piebaldism, a pigmentation defect, and c-KIT mutations have also been found in mast cell leukemias.

Rather than simply repeating the Tyrp experiment with a MGF-specific probe, the screening method was adapted to allow simultaneous identification of mice carrying mutations in MGF and in Tyrp. This involved preparing a number of different probes: (1) a probe for the first exon of Tyrp (2) a probe for the second exon of Tyrp (3) a probe for the first exon of c-kit.

These probes were prepared as before, but the PCR primers used to prepare the Tyrp probes were labeled with biotin at their 5' ends and the primers used to prepare the cKit probe were labeled at their 5' ends with fluorescein. The labeled probes were mixed together and hybridized under stringent conditions with another set of ten nylon membranes containing heteroduplex-enriched nucleic acid samples.

The sites of hybridization of the Tyrp-1 probes were detected using ELISA incorporating anti-biotin horseradish peroxidase (HRP). The sites of hybridization of the cKit probe were detected using ELISA incorporating anti-fluorescein alkaline phosphatase (AP).

The spots which gave a positive HRP result, indicated by a red coloration, revealed the identity of mice carrying heterozygous mutations within either the first or second exon of the Tyrp-1 gene. The same four mice as previously detected gave positive results, along with two further mice (K8 & M3). These mice were subsequently shown to carry heterozygous mutations in the second exon.

The spots which gave a positive AP result, indicated by a blue coloration, were M5 and O14. Analysis of the mice from which these two samples were derived shows that they carried heterozygous mutations in the first exon of the c-kit gene.

It will, of course, be appreciated that any suitable form of differential labeling could have been used to distinguish between mutations in the different genes. The three pairs of PCR primers could, for instance, have been labeled with differently colored fluorochromes. Furthermore, by combining this system with a pair of $^{32}P$ labeled primers for a further gene, for example, four genes could be screened simultaneously etc.

Figure 5:
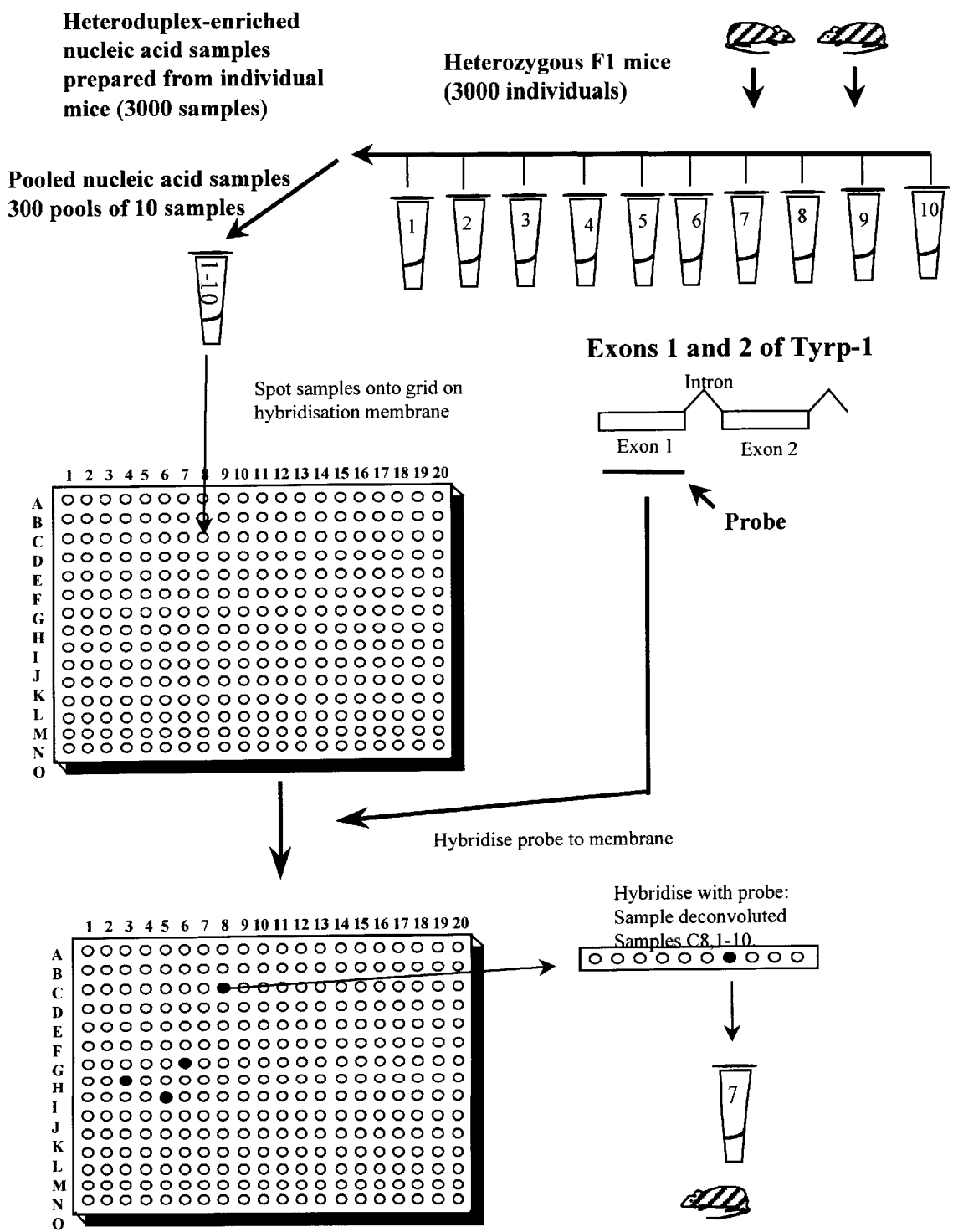
FIG. 5 illustrates how pooling is used according to the invention.

EXAMPLE 3
Screening with Pooling (FIG. 5)

While the screening method use above offers significant advantages when compared with traditional methods, ten nylon membranes were used per experiment. To reduce the effort required to screen the population, heteroduplex-enriched nucleic acid samples were pooled. Prior to spotting on nylon membranes, such samples were combined from groups often mice. This gave 300 pooled samples, rather than 3000 individual samples.

These samples were probed as before with the $^{32}P$ probe for the first exon of the Tyrp gene. Four positive spots were detected [C8, G6, H3, I5]. To deconvolute the pooling, the ten samples which were combined to give sample C8 were then spotted individually on a small nylon membrane. This was probed and one spot gave a positive signal. The mouse from which this sample was derived turned out to be mouse C5.

EXAMPLE 4
Paired Samples

In a further series of experiments, another 1500 F1 mice were bred carrying heterozygotic mutations. At 6 weeks of age, however, these mice were sacrificed. Gametes (sperm or ova) and somatic tissue (spleen, kidney, heart and brain) were harvested from each F1 mouse. CDNA was prepared from the somatic tissue, although genomic DNA could have been used instead. The cDNA from the different organs was combined to give a single combined cDNA sample for each F1 mouse. The gametes were stored in labeled cryo-tubes in five 30×10 racks at −196° C. and somatic tissue CDNA was stored in similar racks at −70° C. Each position in a gamete rack corresponded to a position in a somatic rack which contained material taken from the same mouse.

The five somatic tissue cDNA racks were removed from storage, spotted onto a filter, and probed with the Tyrp first exon probe in the same way as before. Two positive signals were seen, and the gametes corresponding to these somatic tissue samples were removed from the freezer. The gametes were used to produce F2 offspring for study, as described above.

USE

The invention is of use in facilitating the generation and isolation of mutations in a gene or genes of interest.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method for preparing a heteroduplex-enriched nucleic acid sample from an organism carrying heterozyygous mutations, comprising the steps of:

(a) denaturing substantially all of the double-stranded nucleic acid present in a nucleic acid sample from an organism;

(b) allowing the nucleic acid to anneal the under conditions which permit formation of heteroduplexes and homoduplexes; and (c) removing homoduplexes from the annealed sample wherein the removal of said homoduplexes is effected using immobilized mismatch binding proteins (MBP), thereby retaining heteroduplexes in said sample.

2. The method according to claim 1, wherein said organism is a mouse.

3. The method according to claim 1, further comprising prior to step (a) the step of fragmenting the nucleic acid in the sample.

4. The method according to claim 1, wherein the removal of homoduplexes is effected using immobilized MutS protein.

5. The method according to claim 1, further comprising prior to step (a) the steps of: exposing the germ cells of a first parent organism to mutagenic conditions; and mating the first parent organism to a second parent organism to produce an offspring organism carrying heterozygous mutations.

6. A sample of nucleic acid heteroduplexes obtained by the method of claim 5, wherein the frequency of mutation carried in the offspring organism is higher than that of spontaneous mutation.

7. A method for screening a population of organisms carrying heterozygous mutations in order to identify an organism of the population which carries a mutation in a gene of interest, comprising the steps of i. preparing a plurality of samples of nucleic acid from a corresponding plurality of organisms of a population according to the method of claim 1 to produce a plurality of samples, and ii. contacting the plurality of samples with a probe specific for a gene of interest so as to identify a mutation in a gene of interest in an organism containing a mutation.

8. The method according to claim 7, wherein said plurality of organisms comprises 100 or more organisms.

9. The method according to claim 7, wherein said samples are affixed at defined positions to a solid support prior to said contacting step.

10. The method of claim 3, wherein the fragments of the nucleic acid in the sample are 200 to 400 base pairs in length.

* * * * *